United States Patent
Watanabe et al.

(10) Patent No.: US 6,897,953 B2
(45) Date of Patent: May 24, 2005

(54) METHOD FOR MEASURING FLUORESCENCE, APPARATUS FOR MEASURING FLUORESCENCE AND APPARATUS FOR EVALUATING SAMPLE USING IT

(75) Inventors: Motoyuki Watanabe, Hamamatsu (JP); Kazuya Iguchi, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 257 days.

(21) Appl. No.: 10/276,979

(22) PCT Filed: Jun. 7, 2001

(86) PCT No.: PCT/JP01/04794

§ 371 (c)(1),
(2), (4) Date: Nov. 21, 2002

(87) PCT Pub. No.: WO01/94919

PCT Pub. Date: Dec. 13, 2001

(65) Prior Publication Data

US 2003/0151000 A1 Aug. 14, 2003

(30) Foreign Application Priority Data

Jun. 8, 2000 (JP) .......................................... 2000-172454

(51) Int. Cl.⁷ ................................ G01J 3/30; H01J 5/08
(52) U.S. Cl. .................. 356/317; 250/458.1; 250/459.1; 702/32
(58) Field of Search ................................ 356/317, 318, 356/417; 250/461.1, 459.1; 702/32; 422/82.07, 82.08

(56) References Cited

U.S. PATENT DOCUMENTS

| | | | |
|---|---|---|---|
| 4,600,306 A | 7/1986 | Hara et al. .................. 356/317 |
| 4,855,930 A | 8/1989 | Chao et al. .................. 364/497 |
| 5,315,993 A | 5/1994 | Alcala ........................ 128/634 |
| 5,548,124 A * | 8/1996 | Takeshima et al. ...... 250/458.1 |
| 6,121,053 A * | 9/2000 | Kolber et al. ................ 436/172 |

FOREIGN PATENT DOCUMENTS

| | | |
|---|---|---|
| DE | 196 34 873 A1 | 3/1998 |
| EP | 0 420 611 A2 | 4/1991 |
| GB | 2 231 958 A | 11/1990 |
| JP | 5-72049 | 4/1984 |
| JP | 2-268255 | 11/1990 |
| JP | 2911167 | 4/1999 |

* cited by examiner

Primary Examiner—Layla Lauchman
(74) Attorney, Agent, or Firm—Morgan, Lewis & Bockius LLP

(57) ABSTRACT

In a fluorescence measuring method and apparatus, a sample S is irradiated with pulsed pumping light supplied from a pumping light source. Fluorescence generated by the sample S is detected by a photodetector by way of a condensing optical system and a spectroscope. The fluorescence time waveform is subjected to a data analysis in a data processing unit in a controller. This computes waveform data and physical quantities such as fluorescence lifetime. The pumping light time waveform is fixedly arranged with respect to a time axis used for data analysis. Fitting calculations are carried out while moving the fluorescence time waveform and fitting range from an initial position earlier than a pumping light peak to a later end position, and optimal measurement waveform data is selected according to a predetermined selection criterion. Waveform data is thus computed accurately and efficiently regardless of fluctuations in the fluorescence time waveform.

13 Claims, 8 Drawing Sheets

METHOD FOR MEASURING FLUORESCENCE, APPARATUS FOR MEASURING FLUORESCENCE AND APPARATUS FOR EVALUATING SAMPLE USING IT

TECHNICAL FIELD

The present invention relates to fluorescence measuring method and apparatus for measuring the time waveform of fluorescence released from a sample pumped with pumping light and carrying out a data analysis so as to compute waveform data and the like, and a sample evaluating apparatus using the same.

BACKGROUND ART

In a fluorescence measuring apparatus which measures, in a time-resolved manner, fluorescence generated in a sample, so as to acquire information such as fluorescence lifetime, the sample is pumped upon irradiation with pulsed pumping light from a pumping light source, and the fluorescence generated by and emitted from the pumped sample, the change in its intensity along with a lapse of time in particular, is detected by a photodetector such as photomultiplier. Then, the time waveform of fluorescence obtained by the fluorescence detection data outputted from the photodetector is subjected to a data analysis such as arithmetic operation executed in a data processing unit, so as to compute waveform data, fluorescence lifetime, and the like.

The time waveform of fluorescence obtained in such a fluorescence measuring apparatus becomes a fluorescence decay time waveform in which the intensity of fluorescence released after irradiation with pumping light pulses decays with time. In practice, however, the fluorescence time waveform is measured in a state where the exponential fluorescence decay time waveform derived from a fluorescent component and the time waveform of pumping light caused by the time waveform of apparatus response such as the finite pulse width of pumping light resulting from the apparatus are convoluted with each other.

Therefore, when computing waveform data, fluorescence lifetime, and the like by carrying out a data analysis, the fluorescence decay and apparatus response time waveforms are deconvoluted from each other by using the pumping light time waveform measured separately from the measured fluorescence time waveform. At the same time, the fluorescence decay time waveform is subjected to a fitting calculation employing a function system such as exponential function, so as to compute waveform data for specifying the time waveform and physical quantities such as fluorescence lifetime (see, for example, Japanese Patent Publication No. 2911167).

DISCLOSURE OF THE INVENTION

The respective time waveforms of fluorescence and pumping light employed for the above-mentioned data analysis including the fitting calculation are normally measured by using the same measuring system, i.e., the same optical system, photodetector, and the like, in order to prevent the time waveforms from being affected by differences in the configuration of measuring systems. Here, these time waveforms are determined by measuring the fluorescence and pumping light at respective times different from each other. When separate measurement operations are carried out by using the same measuring system as such, the fluctuation in time waveform occurring due to the drift in operating states of the measuring apparatus along with the lapse of time therebetween may become a problem in terms of data analysis.

Recently, in particular, fluorescence measuring apparatus for acquiring information such as fluorescence lifetime have been in the process of being applied to various fields of sample evaluations such as crystal quality evaluation for semiconductor wafers. Also, as the application field for such a fluorescence measuring apparatus expands, there has been occurring a necessity to carry out a number of fluorometric operations continuously in a time as short as possible, for example, so as to evaluate a plurality of parts on a semiconductor wafer by fluorometry.

Here, measurement conditions in each fluorometric operation change with time due to such phenomena as the change in operating state of the measuring apparatus caused by heat and the like, and the fluctuation in oscillation timing of a pulse laser light source employed as a pumping light source from the timing of clock signals for synchronization with the photodetector. Therefore, if the respective fluorescence time waveforms obtained at separate fluorometric operations are used as they are, the position of fluorescence time waveform on the time axis may shift from the pumping light time waveform determined by a separate measurement operation beforehand among the fluorometric operations.

As the measured fluorescence time waveform thus shifts on the time axis of data analysis and from the pumping light time waveform fixed with respect to the time axis, data analyses such as fitting calculation by deconvolution may not be carried out correctly due to the shift in time, whereby the waveform data and fluorescence lifetime cannot be computed accurately. If the pumping light measurement is to be carried out each time when fluorometry is conducted, the time required for fluorometry and sample evaluation may become longer while the influence of shift of time waveform is suppressed.

In view of the foregoing problems, it is an object of the present invention to provide fluorescence measuring method and apparatus which can compute waveform data and the like correctly and efficiently regardless of fluctuations in fluorescence time waveforms, and a sample evaluating apparatus using the same.

For achieving such an object, the fluorescence measuring method of the present invention comprises (1) a pumping step of irradiating a sample with pulsed pumping light; (2) a light-detecting step of detecting fluorescence released from the sample pumped with the pumping light; and (3) a data processing step of subjecting a time waveform of fluorescence detected by the light-detecting step to a data analysis including a fitting calculation in a fitting range acting as a predetermined time range fixedly set for the time waveform of fluorescence so as to compute waveform data; (4) wherein, in the data processing step, a time waveform of pumping light determined beforehand and the time waveform of fluorescence are arranged on a time axis used for the fitting calculation such that a fluorescence peak of the time waveform of fluorescence is placed at an initial position earlier or later by a predetermined time width than a time position substantially coinciding with a pumping light peak of the time waveform of pumping light, and then, while moving the time waveform of fluorescence and fitting range or the time waveform of pumping light with respect to the time axis to an end position on the time axis on the opposite side of the time position where the fluorescence peak substantially coincides with the pumping light peak from the initial position, respective fitting calculations are carried out at a plurality of time positions different from each other with reference to the time waveform of pumping light, and a waveform data item selected according to a predetermined selection criterion from a plurality of waveform data items respectively computed in the fitting calculations is employed as final measurement waveform data.

The fluorescence measuring apparatus of the present invention comprises (a) pumping means for irradiating a sample with pulsed pumping light; (b) light-detecting means for detecting fluorescence released from the sample pumped with the pumping light; and (c) data processing means for subjecting a time waveform of fluorescence detected by the light-detecting means to a data analysis including a fitting calculation in a fitting range acting as a predetermined time range fixedly set for the time waveform of fluorescence so as to compute waveform data; (d) wherein the data processing means arranges a time waveform of pumping light determined beforehand and the time waveform of fluorescence on a time axis used for the fitting calculation such that a fluorescence peak of the time waveform of fluorescence is placed at an initial position earlier or later by a predetermined time width than a time position substantially coinciding with a pumping light peak of the time waveform of pumping light, and then, while moving the time waveform of fluorescence and fitting range or the time waveform of pumping light with respect to the time axis to an end position on the time axis on the opposite side of the time position where the fluorescence peak substantially coincides with the pumping light peak from the initial position, carries out respective fitting calculations at a plurality of time positions different from each other with reference to the time waveform of pumping light, and employs a waveform data item selected according to a predetermined selection criterion from a plurality of waveform data items respectively computed in the fitting calculations as final measurement waveform data.

In the above-mentioned fluorescence measuring method and apparatus, a fluorescence time waveform and a pumping light time waveform measured separately from fluorometry are respectively arranged at predetermined time positions on the time axis for a fitting calculation. Then, the fluorescence time waveform or pumping light time waveform is moved from the initial position where the fluorescence peak is located earlier or later by a predetermined time width than the pumping light peak, to the end position on the opposite side (from the earlier initial position to the later end position or from the later initial position to the earlier end position).

If there is no shift in thus measured fluorescence time waveform in the time-axis direction here, so that the respective positions (time positions) of fluorescence and pumping light time waveforms on the time axis coincide with each other, the fluorescence peak in the fluorescence time waveform will be located at the time position of the pumping light peak or later. Therefore, if the initial and end positions for specifying the range for mutually moving the fluorescence and pumping light time waveforms in a data analysis are appropriately set on the time axis, the above-mentioned fluorescence time waveform position at the time when there is no shift will always be included in the moving range.

In the fluorescence measuring method and apparatus in accordance with the present invention, by contrast, a plurality of fitting calculations are executed while moving the time waveform of fluorescence or pumping light on the time axis as mentioned above, so as to determine a plurality of waveform data items from a single fluorescence time waveform, and an optimal measurement waveform data item is selected from a plurality of waveform data items while using as a selection criterion an amount to become a determination criterion for determining whether the result of fitting calculation is favorable or not or the like. This makes it possible to compute waveform data, individual physical quantities, and the like efficiently with a sufficient accuracy regardless of whether the fluorescence time waveform shifts or not.

In the data analysis, the time range (fitting range) for specifying the data range for carrying out fitting is set to a fixed time position with respect to the fluorescence time waveform instead of the time axis. When moving the fluorescence time waveform, the fitting range is moved on the time axis together with the fluorescence time waveform, so as to execute respective fitting calculations. As a consequence, each of a plurality of fitting calculations executed is always carried out under an optimal condition.

Preferably, in the plurality of fitting calculations within the moving range of fluorescence or pumping light time waveform, the moving interval on the time axis for executing the fitting calculations and the like are appropriately set according to the numerical accuracy required for waveform data and physical quantities and the like. As for the initial and end positions, the initial position is specified according to the time width from the pumping light peak and the like. The end position may be set according to the time width from the pumping light peak as with the initial position, or determination based on the selection criterion may be carried out each time the fitting calculation is executed and the time position where the waveform data to be selected is determined may be used as the end position so as to terminate the data analysis.

The sample evaluating apparatus in accordance with the present invention comprises the above-mentioned fluorescence measuring apparatus, and sample evaluating means for evaluating the sample by comparing the measurement waveform data obtained by the data processing means of the fluorescence measuring apparatus and reference waveform data determined beforehand with each other.

This realizes a sample evaluating apparatus which can evaluate a sample accurately and efficiently even when the measured fluorescence time waveform shifts on the time axis. In apparatus for evaluating semiconductor wafers and the like, in particular, a number of fluorometric operations are repeatedly executed for individual parts of a sample (semiconductor wafer). Even in such a case, employing the above-mentioned fluorescence measuring apparatus can minimize the influence of shift in the fluorescence time waveform caused by fluctuations in measurement conditions occurring between the individual fluorometric operations.

Thus configured sample evaluating apparatus can be employed not only for the above-mentioned semiconductor wafer quality evaluation, but also for various sample evaluations such as mass-screening in drug developments.

BEST MODES FOR CARRYING OUT THE INVENTION

Figure 1:
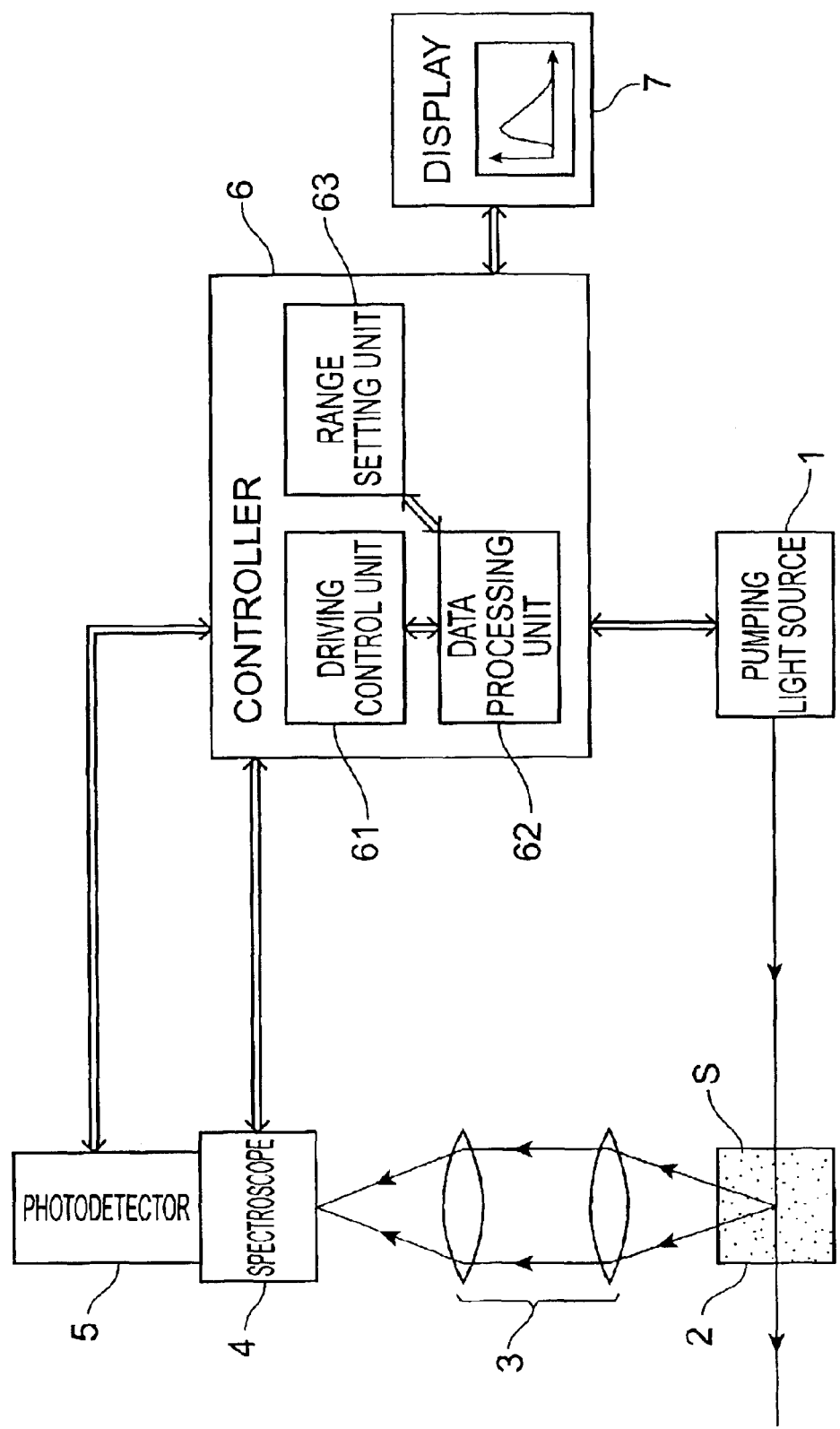
FIG. 1 is a diagram showing an embodiment of fluorescence measuring apparatus.

In the following, preferred embodiments of fluorescence measuring method and apparatus in accordance with the present invention, and a sample evaluating apparatus using the same will be explained in detail with reference to the drawings. In the explanation of the drawings, constituents identical to each other will be referred to with numerals identical to each other without repeating their overlapping descriptions. Ratios of dimensions in the drawings do not always match those explained.

FIG. 1 is a diagram showing an embodiment of the fluorescence measuring apparatus in accordance with the present invention. This fluorescence measuring apparatus comprises a pumping light source 1 for irradiating a sample S held by a sample holding means 2 with pumping light, a photodetector 5 for detecting fluorescence released from the sample S pumped with the pumping light, and a controller 6 for driving and controlling the pumping light source 1 and the photodetector 5. In FIG. 1, the sample S in a gaseous form or the like held within a sample cell placed as the sample holding means 2 is shown as an example of the sample S.

As the pumping light source 1, a pulse light source which can supply pulsed light having a predetermined wavelength and time width as pumping light is used. Employed as the photodetector 5 is one such as photomultiplier (PMT) or streak camera, for example, which is capable of time-resolved measurement for obtaining time waveforms.

Placed between the sample holding means 2 holding the sample S and the photodetector 5 are a condensing optical system 3 and a spectroscope 4. The condensing optical system 3 has necessary optical elements such as lenses, and condenses and converges onto the photodetector 5 the fluorescence generated in pumped parts within the sample S pumped with the pumping light emitted from the pumping light source 1 and released into various directions.

The spectroscope 4 is placed as wavelength selecting means for selecting an optical component in a predetermined wavelength region in the optical components detected by the photodetector 5 and making thus selected optical component incident on the photodetector 5. As such wavelength selecting means, not only a spectroscope but also a wavelength selecting filter or the like can be used. The wavelength region of light to be selected by wavelength selecting means such as the spectroscope 4 or wavelength selecting filter is appropriately set or changed to a wavelength region including the wavelength of fluorescence or pumping light to be detected by the photodetector 5.

The controller 6 for controlling operations of individual parts of the fluorescence measuring apparatus and the like has a driving control unit 61, a data processing unit 62, and a range setting unit 63. Employable as such a controller 6 is a personal computer (PC), for example, which invokes control software, data processing software, and the like, thereby realizing individual functions necessary as the controller 6.

The pumping light source 1, the spectroscope 4, and the photodetector 5 are driven by clock signals and other control signals supplied from the driving control unit 61 of the controller 6. As a consequence, with respect to the pulsed pumping light supplied from the pumping light source 1 at predetermined clock time intervals, the fluorescence released from the sample S upon irradiation with the individual pumping light pulses and its change with time are detected by the photodetector 5. The fluorescence detection data based on thus detected fluorescence is fed into the controller 6 according to the detection signals.

According to data analysis instructions based on clock signals and the like from the driving control unit 61, the data processing unit 62 executes data processing such as necessary signal processing and data analysis with respect to the detection signals inputted from the photodetector 5. Initially, in the data analysis with respect to the fluorescence detection data, the fluorescence time waveform indicative of the temporal change in the fluorescence intensity is determined for the fluorescence released from the sample S and detected by the photodetector 5 due to pumping light pulses corresponding thereto.

Thus obtained fluorescence time waveform is subjected to a data analysis including a fitting calculation in which the time waveform is fitted with a predetermined curve (function system) or the like, so as to compute waveform data, necessary physical quantities, and the like. Examples of thus computed waveform data and physical quantities include physical quantities such as individual parameters for determining the curved form of time waveform, fluorescence lifetime of fluorescent components, and fluorescence intensity. The range setting unit 63 sets the time range of fitting (hereinafter referred to as fitting range) used for fitting calculations in the data processing unit 62. A specific data analysis method, setting of the fitting range, and the like will be explained later.

Preferably, a display 7 (see FIG. 1) for displaying the fluorescence time waveform obtained by the data processing unit 62, the computed waveform data, the fluorescence lifetime, and the like is connected to the controller 6 as necessary.

When pulsed pumping light is supplied from the pumping light source 1 and irradiates the sample S (pumping step) in the foregoing configuration, thus pumped sample S releases fluorescence, which is then detected by the photodetector 5 by way of the condensing optical system 3 and spectroscope 4 (light-detecting step). Thereafter, in the data processing unit 62 of the controller 6, a data analysis is carried out for thus measured fluorescence time waveform, so as to compute waveform data and the like (data processing step).

A fluorescence measuring method in the fluorescence measuring apparatus shown in FIG. 1 will now specifically be explained while illustrating its data analysis method (data processing method).

First, the fluorescence time waveform obtained by the fluorescence measurement after the pumping light pulse irradiation will be explained.

Figure 2:
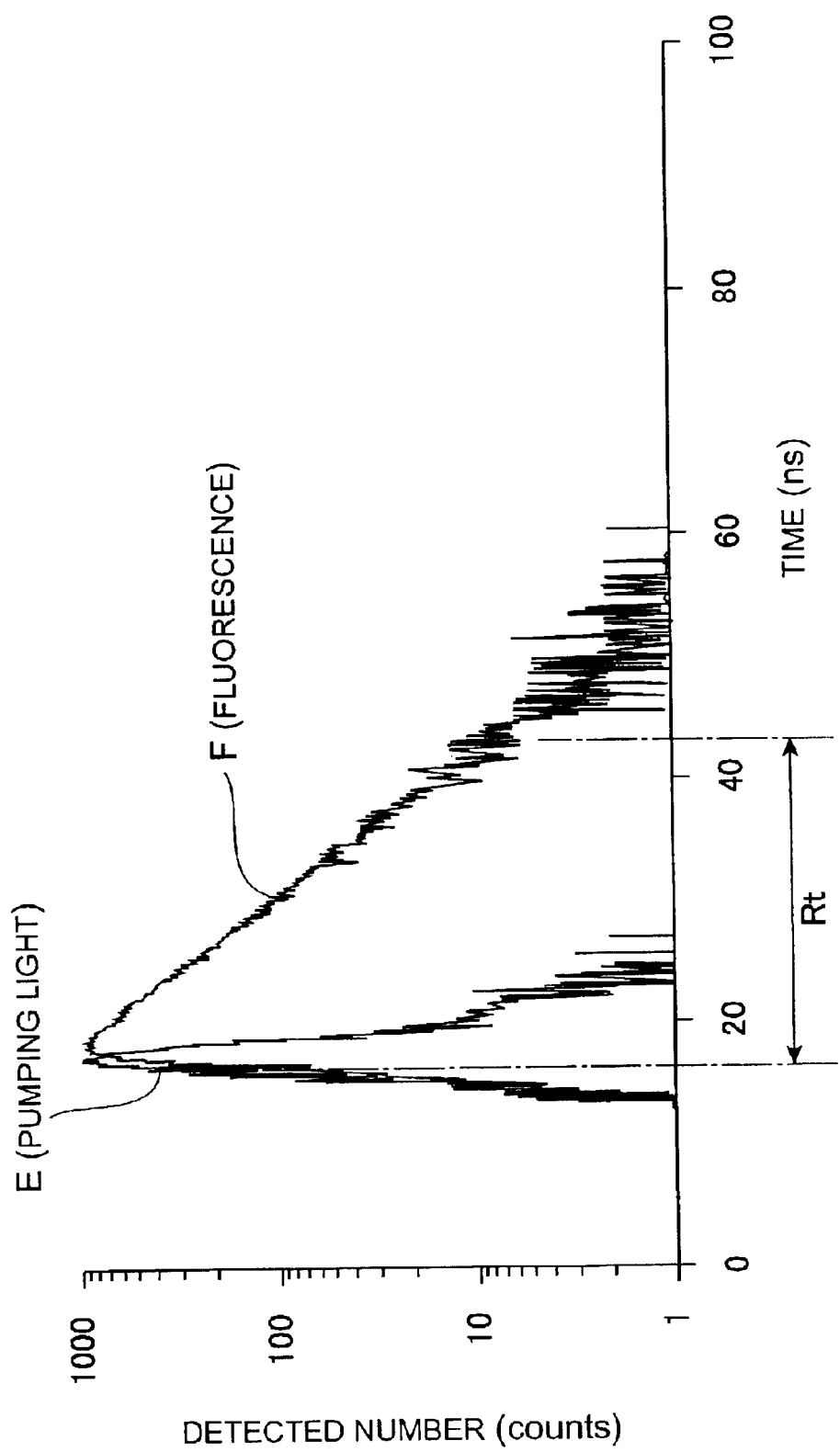
FIG. 2 is a graph showing an example of pumping light and fluorescence time waveforms.

FIG. 2 is a graph showing an example of the time waveform of pumping light emitted from the pumping light source 1 to the sample S and the time waveform of fluorescence released from the sample S after the pumping light pulse irradiation. In this graph, the abscissa indicates the time axis (ns) used for the data analysis, whereas the ordinate indicates the detected number (counts; detected intensity) of pumping light or fluorescence. Here, in conformity to the fact that the time waveform of fluorescence decay is exponential, the detected number in the ordinate corresponding to the fluorescence intensity is indicated by log scale. The time axis on the abscissa corresponds to the lapse of time at the time of measuring fluorescence or pumping light.

Here, the pumping light time waveform shown in FIG. 2 in addition to the fluorescence time waveform is one to be referred to in the data analysis of fluorescence time waveform as will be explained later. For preventing differences in the configuration of measuring systems from affecting time waveforms, the pumping light time waveform is normally measured by using the same measuring system, i.e., the same optical system, photodetector, and the like, used for fluorometry.

In the configuration shown in FIG. 1, pumping light can be measured by the photodetector 5 by way of the condensing optical system 3 and spectroscope 4, for example, when the sample holding means 2 holds a scatterer, which generates no fluorescence, in place of the sample S to be subjected to fluorometry. Alternatively, a separate optical system for guiding a part of pumping light to the photodetector may be provided. As for the wavelength selection effected by the spectroscope 4 (or a wavelength selecting filter and the like), since the pumping light and fluorescence have respective wavelengths different from each other, it is necessary that the pumping light measurement be carried out while changing the wavelength region to be selected.

When a sample is pumped with pulsed pumping light, the fluorescence intensity of fluorescence released from the sample indicates the temporal change of fluorescence decaying with time after the pumping light irradiation. The fluorescence time waveform caused by the change in time becomes an exponential fluorescence decay time waveform in the case where the time width of pumping light pulse is negligible. Then, from the amplitude and attenuation factor of the exponential decay curve, the fluorescence intensity and fluorescence lifetime of the fluorescence pumped in the sample can be calculated.

On the other hand, the fluorescence time waveform actually measured in the fluorescence measuring apparatus is one deformed from an ideal decay curve to some extent due to influences caused by apparatus response. Namely, the fluorescence time waveform is obtained in a state where the above-mentioned exponential fluorescence decay time waveform resulting from the temporal change of fluorescence itself is convoluted with the pumping light time waveform determined by the finite pulse time width of pumping light, the shift in time depending on the optical path, and the like.

In the example of time waveforms shown in FIG. 2, the pumping light time waveform E indicates the pumping light pulse having a pulse time width of about several nanoseconds which cannot be neglected. By contrast, the fluorescence time waveform F is convoluted with such a pumping light time waveform E, whereby its detected number rises together with the starting of pumping light supply, and increases until the fluorescence intensity reaches a peak at a certain point in time (hereinafter referred to as fluorescence peak), after which the fluorescence intensity decays substantially exponentially (linearly in the log scale). Here, the time position of the fluorescence peak on the time axis is located at the time position of the pumping light intensity peak (hereinafter referred to as pumping light peak) in the pumping light time waveform or later as shown in FIG. 2.

A data analysis method for computing the waveform data, fluorescence lifetime, and the like from the fluorescence time waveform will now be explained.

In order to acquire information such as waveform data and fluorescence lifetime by carrying out a data analysis with respect to the fluorescence time waveform F convoluted with the pumping light time waveform E as mentioned above, it is necessary that a data analysis including a fitting calculation by deconvolution be carried out by using the pumping light time waveform E and a fluorescence decay time waveform assumed by appropriate function system (e.g., exponential function) and parameters (e.g., amplitude and attenuation factor).

In this data analysis, a fitting calculation (deconvolution operation) isolates the component of pumping light time waveform E convoluted with the fluorescence time waveform F, so as to extract the fluorescence decay time waveform. Then, according to the result of fitting calculation with respect to the fluorescence decay time waveform, not only waveform data such as amplitude and attenuation factor, but also physical quantities such as fluorescence intensity and fluorescence lifetime are computed.

The above-mentioned fitting calculation with respect to the fluorescence time waveform F is executed while setting on the time axis a fitting range which is a time range for specifying detection data used for the fitting calculation in the measured fluorescence time waveform F. As an example of such a fitting range, FIG. 2 shows a time range Rt set with respect to the fluorescence time waveform F.

Here, the operating state of the fluorescence measuring apparatus may drift during the measurement along with the lapse of time from the measurement of the pumping light time waveform used for deconvolution to the fluorescence measurement or the lapse of time while executing a plurality of fluorometric operations to be carried out repeatedly. In this case, the fluctuation of fluorescence time waveform caused by the change in apparatus state between the individual fluorometric operations may become problematic in terms of data analysis.

When a pulse laser light source is used as the pumping light source 1, for example, its oscillation timing may vary within a certain level of time range with respect to clock signals for synchronous driving supplied from the driving control unit 61 of the controller 6. In this case, the pumping light irradiation timing for the sample S shifts from the clock signal timing, whereby the time position of time waveform on the time axis shifts with respect to the fluorescence generated upon the pumping light pulse irradiation as well.

Figure 3:
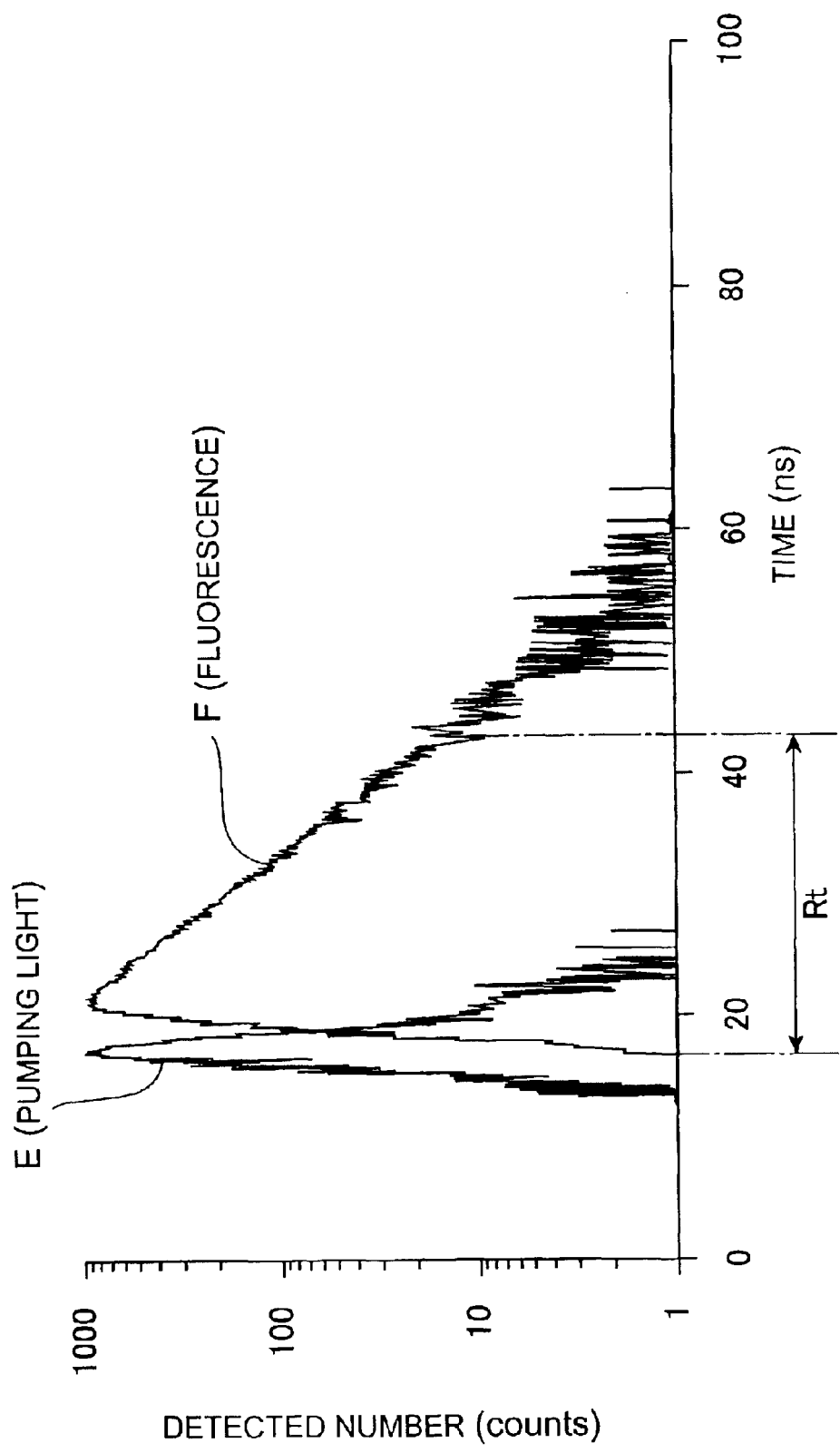
FIG. 3 is a graph showing another example of pumping light and fluorescence time waveforms.

FIG. 3 shows the pumping light and fluorescence time waveforms in the case where such a fluorescence time waveform shift is generated. The pumping light time waveform E is arranged at a fixed time position with respect to the time axis used for a fitting calculation so as to be located at a time position corresponding to the fluorescence time waveform F (see FIG. 2) in the case with no time waveform shift in the data analysis of fluorescence time waveform F carried out for each fluorometric operation. Here, if the fluorescence time waveform F is measured while being shifted to the earlier or later side on the time axis as shown in FIG. 3, the pumping light time waveform E and the fluorescence time waveform F will deviate from each other on the time axis, whereby the deconvolution operation cannot be carried out correctly. Also, it will be problematic in terms of executing the fitting calculation if the fitting range Rt is set to a time range fixed with respect to the time axis, since the fitting range Rt and the fluorescence time waveform F similarly deviate from each other.

By contrast, the fluorescence measuring apparatus of the embodiment shown in FIG. 1 and the fluorescence measuring method carried out thereby sequentially execute a plurality of fitting calculations for a data analysis at respective time positions different from each other while moving both of the fluorescence time waveform F and fitting range Rt with respect to the time axis. Then, from a plurality of waveform data items respectively computed in the fitting calculations, an optimal waveform data item is selected as final measurement waveform data, so as to realize a data analysis minimizing the influence of fluctuations in time waveforms in individual fluorometric operations such as the above-mentioned shift in fluorescence time waveform F.

FIGS. 4A to 4D are schematic charts for explaining the data analysis method in the fluorescence measuring method using the fluorescence measuring apparatus shown in FIG. 1. Here, in each of the schematic graphs shown in FIGS. 4A to 4D, the abscissa indicates the time axis t of the data analysis (corresponding to the lapse of time in measurement), whereas the ordinate indicates the detected numbers of pumping light and fluorescence (corresponding to the pumping light intensity and fluorescence intensity) by log scale.

In each of FIGS. 4A to 4D, for simplifying the explanation and illustration, the pumping light time waveform E is indicated by a pulsed waveform neglecting the pulse time width whereas the fluorescence time waveform F is indicated by a triangular waveform whose rise and decay each become linear in log scale. As for the pumping light waveform E, the time position where the pumping light peak is fixed on the time axis is defined as t0.

Figure 4A:
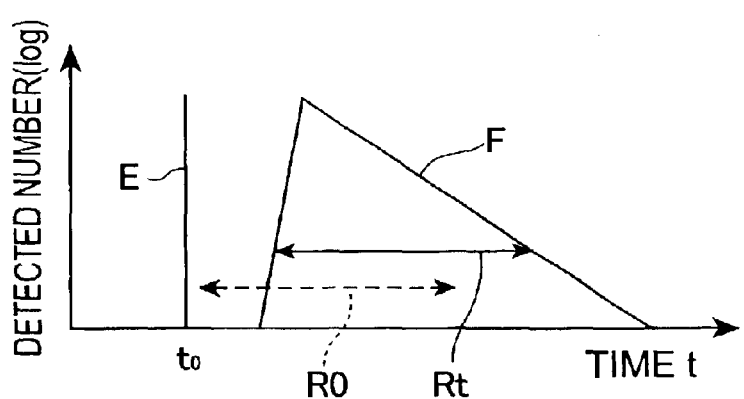
FIGS. 4A to 4D are schematic charts for explaining a data analysis method in the fluorescence measuring apparatus shown in FIG. 1.

FIG. 4A shows the state where the fluorescence time waveform F is measured as being shifted to the "+" direction (positive direction) of the time axis with respect to the time axis used for the fitting calculation and the pumping light time waveform E fixedly arranged with respect to the time axis. If the fitting range used for the fitting calculation in the data analysis is set to a time range R0 (dotted line) fixed with respect to the time axis in this case, the fluorescence time waveform F will deviate from the fitting range R0 as the time waveform shifts, whereby correct waveform data and physical quantities cannot be obtained as results of the fitting calculations.

In the fluorescence measuring method of this embodiment, by contrast, a fitting range is set as a time range fixed with respect to the fluorescence time waveform F instead of the time axis, as with the time range Rt (solid line) shown in FIG. 4A. The fitting range Rt is set automatically or manually by an operator (range setting step) by using the fluorescence time waveform in the initial fluorometric operation or a preliminary fluorometric operation carried out prior to the actual measurement in the range setting unit 63 of the controller 6 (see FIG. 1).

Figure 4B:
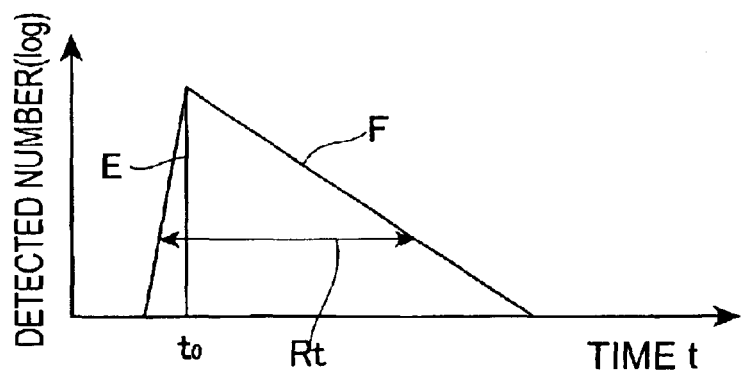
Figure 4C:
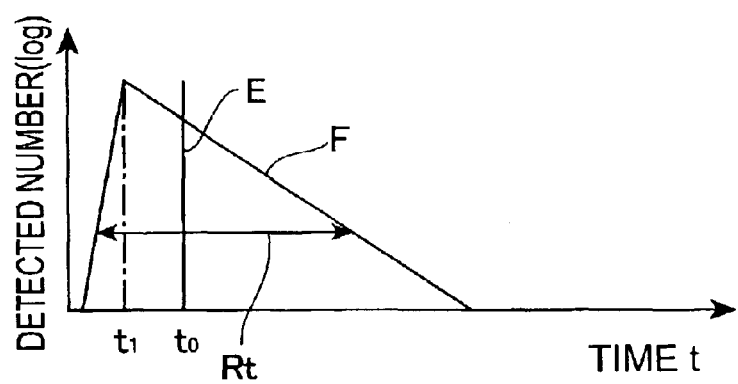

Next, the fluorescence time waveform F measured at the time position shifted from the pumping light time waveform E as shown in FIG. 4A is moved until the respective time positions of the pumping light and fluorescence peaks substantially coincide with each other (FIG. 4B). Then, the fluorescence time waveform F is further moved and arranged such that the fluorescence peak is positioned at an initial position t1 which is earlier by a predetermined time width than the time position t0 substantially coinciding with the pumping light peak (t1<t0) (FIG. 4C).

Figure 4D:
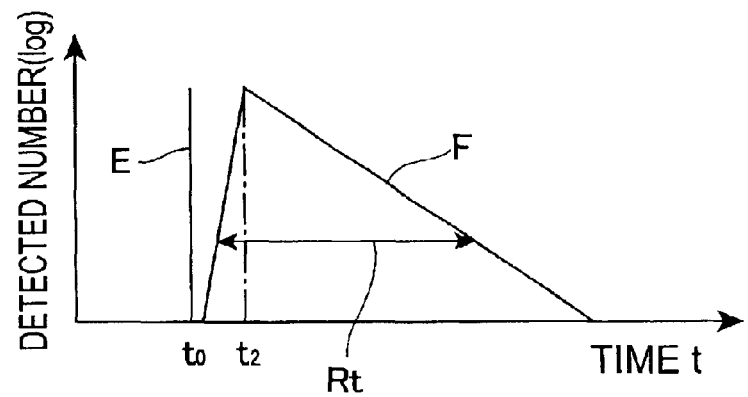

The above-mentioned initial position t1 is the time position to become the start position for a plurality of fitting calculations to be executed in the data analysis. Then, the fluorescence time waveform F is moved from the initial position t1 earlier than the pumping light peak time position t0 to the end position t2 later than the time position t0 (t2>t0) (FIG. 4D).

Here, while the fluorescence time waveform F is sequentially moved from the initial position t1 in the "+" direction at predetermined moving time intervals, a fitting calculation is carried out at each of thus moved time positions, so as to compute waveform data. In this case, since the fitting range Rt is set as a time range fixed with respect to the fluorescence time waveform F as mentioned above, it is moved with respect to the time axis together with the fluorescence time waveform F.

Among the respective waveform data items computed in a plurality of fitting calculations executed at the individual time positions, one selected as optimal according to a predetermined selection criterion is employed as final measurement waveform data with respect to the fluorescence time waveform F. As the selection criterion for waveform data, a quantity acting as a determination criterion for determining whether the result of a fitting calculation executed is favorable or not or the like is used, so as to select the best fitting calculation result, thereby computing final measurement waveform data, and physical quantities such as fluorescence lifetime.

According to the above-mentioned fluorescence measuring apparatus and method, if the initial position t1 and end position t2 specifying the range for moving the fluorescence time waveform at the time of executing a plurality of fitting calculations are appropriately arranged on the time axis, the time position of the fluorescence time waveform F in the case where there is no shift in the time waveform will always be included within the moving range. While moving the fluorescence time waveform F within the moving range, a plurality of fitting calculations are executed, so as to determine a plurality of waveform data items from a single fluorescence time waveform F, and an optimal measurement waveform data item is selected from a plurality of waveform data items according to a predetermined selection criterion. Here, regardless of whether a shift occurs in the fluorescence time waveform or not, waveform data, physical quantities such as fluorescence lifetime, and the like can always be computed efficiently with a sufficient accuracy and numeric precision.

Also, the fitting range Rt employed for each of a plurality of fitting calculations is set as a time range fixed to the fluorescence time waveform F instead of the time axis and, while moving the fitting range Rt as the fluorescence time waveform F moves, the fitting calculation is carried out at each time position (see FIGS. 4C and 4D). As a consequence, each fitting calculation can be executed under a favorable condition.

Preferably, as for the movement of the fluorescence time waveform F from the initial position t1 to the end position t2, moving time intervals on the time axis are appropriately set so as to yield a numerical accuracy required for quantities to be determined such as waveform data and fluorescence lifetime, and the fitting calculation is executed at each of the time positions moved at the moving intervals. Setting the moving time intervals as such can improve the accuracy of each value computed and the efficiency of the data analysis including the fitting calculation at the same time. As a specific example of moving time interval setting methods, if time waveform data is digitized into a plurality of channels, the fitting calculation may be executed each time when the fluorescence time waveform F is moved by 1 ch (channel) or a plurality of channels.

As for the initial position t1 and end position t2, the initial position t1 is specified by the time width from the pumping light peak time position t0 set beforehand. On the other hand, the end position t2 may be set according to the time width or the like from the time position t0 as with the initial position t1, or a determination based on the above-mentioned selection criterion may be carried out each time the fitting calculation is executed, and the data analysis maybe terminated while defining as the end position the time position where the waveform data to be selected is determined.

Preferably, the fitting range Rt employed for the fluorescence time waveform F is set beforehand in the range setting unit 63 of the controller 6. As an example of specific method of setting a fitting range in the range setting unit 63, it may automatically be set from the fluorescence time waveform obtained by the initial fluorometric operation or a preliminary fluorometric operation. Alternatively, while this fluorescence time waveform is displayed on the display 7, the range may manually be set by an operator manipulating a mouse cursor or the like.

A method of setting the fitting range Rt to a time range fixed with respect to the fluorescence time waveform F is configured such that, while the fluorescence time waveform is specified by the time position of the fluorescence peak in the fluorescence time waveform F on the time axis, the fitting range is set with reference to this fluorescence peak. This can set respective favorable fitting ranges for the fluorescence time waveforms obtained by individual measurement operations.

As a specific fitting range, a time range is preferably set so as to exclude the rising and decaying end parts of the time waveforms (both end parts of the time waveform), susceptible to statistical deviations and noise, yielding a smaller detected number of fluorescence. More specifically, for example, there is a method in which the fluorescence intensity of the fluorescence peak is employed as a reference fluorescence intensity, and the start and end points of the fitting range are set by a predetermined range (e.g., at least 20%) in terms of fluorescence intensity % with respect to the reference fluorescence intensity. In another method, the position of the fluorescence peak on the time axis is used as a reference time position, and the start and end points of the fitting range are set according to a predetermined time range determined with respect to the reference time position.

Here, such a fitting range may be set such that both of its start and end positions are located within the decay waveform later than the fluorescence peak, or such that the start point is within the rising waveform earlier than the fluorescence peak whereas the end point is within the decay waveform later than the fluorescence peak.

Figure 5:
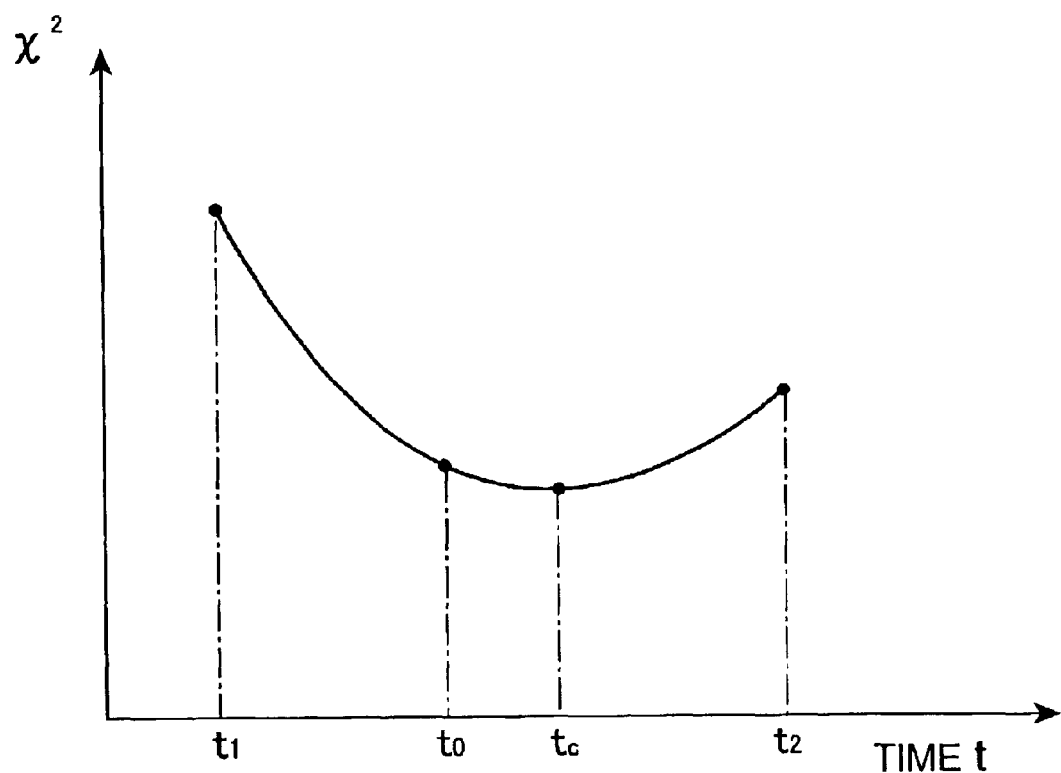
FIG. 5 is a schematic chart for showing how to select a measurement waveform data item from a plurality of waveform data items.

As the selection criterion for selecting the final measurement waveform data from the respective waveform data items computed by a plurality of fitting calculations, $\chi^2$ values determined in the fitting calculations are preferably used. This selecting method will be explained with reference to the graph shown in FIG. 5. FIG. 5 is a schematic chart showing the change in respective $\chi^2$ values obtained in a plurality of fitting calculations carried out from the initial position t1 to the end position t2, in which the abscissa indicates the time position to which the fluorescence time waveform F has moved, whereas the ordinate indicates the respective $\chi^2$ values obtained by the fitting calculations at individual time positions.

The $\chi^2$ value (chi-square value) is a value determined as an index for determining whether the result of calculation of each fitting executed in an approximate calculation such as nonlinear least-squares method used in such a fitting calculation is favorable or not, and becomes a smaller value approximating 1 ($\chi^2 > 1$) as the fitting condition is better. Namely, when fitting calculations are started from the initial position t1 earlier than the time position t0 in the above-mentioned data analysis method, the $\chi^2$ value decreases as the time position of the fluorescence time waveform F moves in the "+" direction. Then, after being minimized at a certain time position tc at the pumping light peak time position or later, the $\chi^2$ value increases again toward the end position t2.

If the waveform data computed by the fitting calculation in which the $\chi^2$ value is minimized, i.e., the waveform data computed by the fitting calculation at the time position tc in FIG. 5, is selected as the final measurement waveform data, an optimal measurement waveform data item can be chosen from a plurality of waveform data items. When the $\chi^2$ value, which is a value determined from a fitting calculation, is used as a determination criterion, a data analysis including waveform data selection can automatically be executed in an efficient manner.

Figure 6:
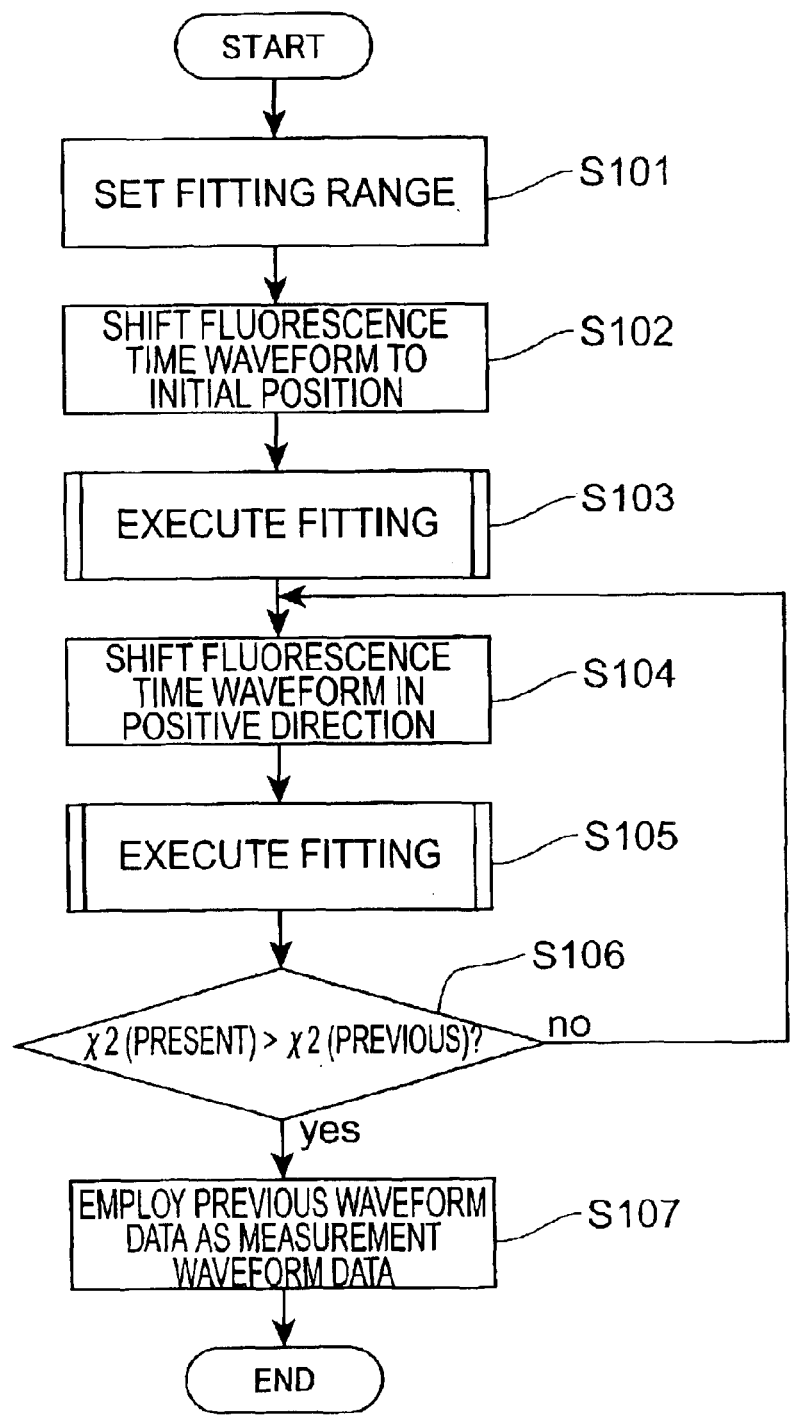
FIG. 6 is a flowchart showing an example of fluorescence measuring method in the fluorescence measuring apparatus shown in FIG. 1.

FIG. 6 is a flowchart showing an example of data analysis method in the case where the $\chi^2$ value obtained by the fitting calculation is used as a criterion for selecting waveform data.

Initially, in this data analysis method, a fitting range is set with respect to the fluorescence time waveform F by a fluorescence intensity % range with reference to the fluorescence peak, a time range, or the like (step S101). Next, the fluorescence time waveform F obtained by measurement is moved on the time axis to the time position t0 where the fluorescence peak substantially coincides with the pumping light peak, and is further moved by a predetermined time width, in the "−" direction, whereby the fluorescence time waveform F is disposed at the initial position t1 (S102). Then, at this initial position t1, the first fitting calculation is executed while employing the above-mentioned fitting range (S103), so as to compute the first waveform data and $\chi^2$ value.

Next, the execution of a plurality of fitting calculations between the initial position t1 and the end position t2 is started. Namely, the fluorescence time waveform F is moved in the "+" direction toward the end position t2 by a predetermined moving time interval (e.g., by +1 ch) (S104), and the next fitting calculation is executed at thus moved time position (S105). Next, the $\chi^2$ value obtained by this fitting calculation is compared with the $\chi^2$ value obtained by the previous fitting calculation (S106).

If the $\chi^2$ value in this operation is not greater than that in the previous operation, the $\chi^2$ value has not reached the minimum value yet (see FIG. 5), whereby the moving of the fluorescence time waveform F (S104) and the fitting calculation (S105) are repeated. If the $\chi^2$ value in this operation is greater than that in the previous operation, the $\chi^2$ value in the previous operation is the minimum value of the respective $\chi^2$ values obtained in a plurality of fitting calculations. Therefore, in this case, the plurality of fitting calculations are terminated, and the waveform data computed in the fitting calculation at the time position of fluorescence time waveform F in the previous operation (e.g. −1 ch) is selected as the final measurement waveform data (S107).

The foregoing data analysis method can compute waveform data and physical quantities such as fluorescence lifetime with respect to the fluorescence time waveform obtained at each fluorometric operation while attaining a sufficient accuracy and data analysis efficiency at the same time regardless of whether a shift occurs in the fluorescence time waveform or not.

The above-mentioned fluorescence measuring apparatus and method can be employed in sample evaluating apparatus for evaluating qualities and the like of various samples.

Recently, fluorescence measuring apparatus (fluorescence lifetime measuring apparatus) have been in the process of being applied to evaluations of semiconductor wafer crystal qualities and the like. When evaluating a semiconductor wafer, it is necessary that the distribution of crystal quality of the semiconductor wafer used in the product be evaluated beforehand within the wafer in order to improve the yield. When a fluorescence measuring apparatus is used for such a quality evaluation, fluorescence lifetime and fluorescence intensity are determined by fluorometry using the semiconductor wafer to be evaluated as a sample and are compared with those in a reference sample, so as to evaluate the crystal quality at each part of the semiconductor wafer.

Figure 7:
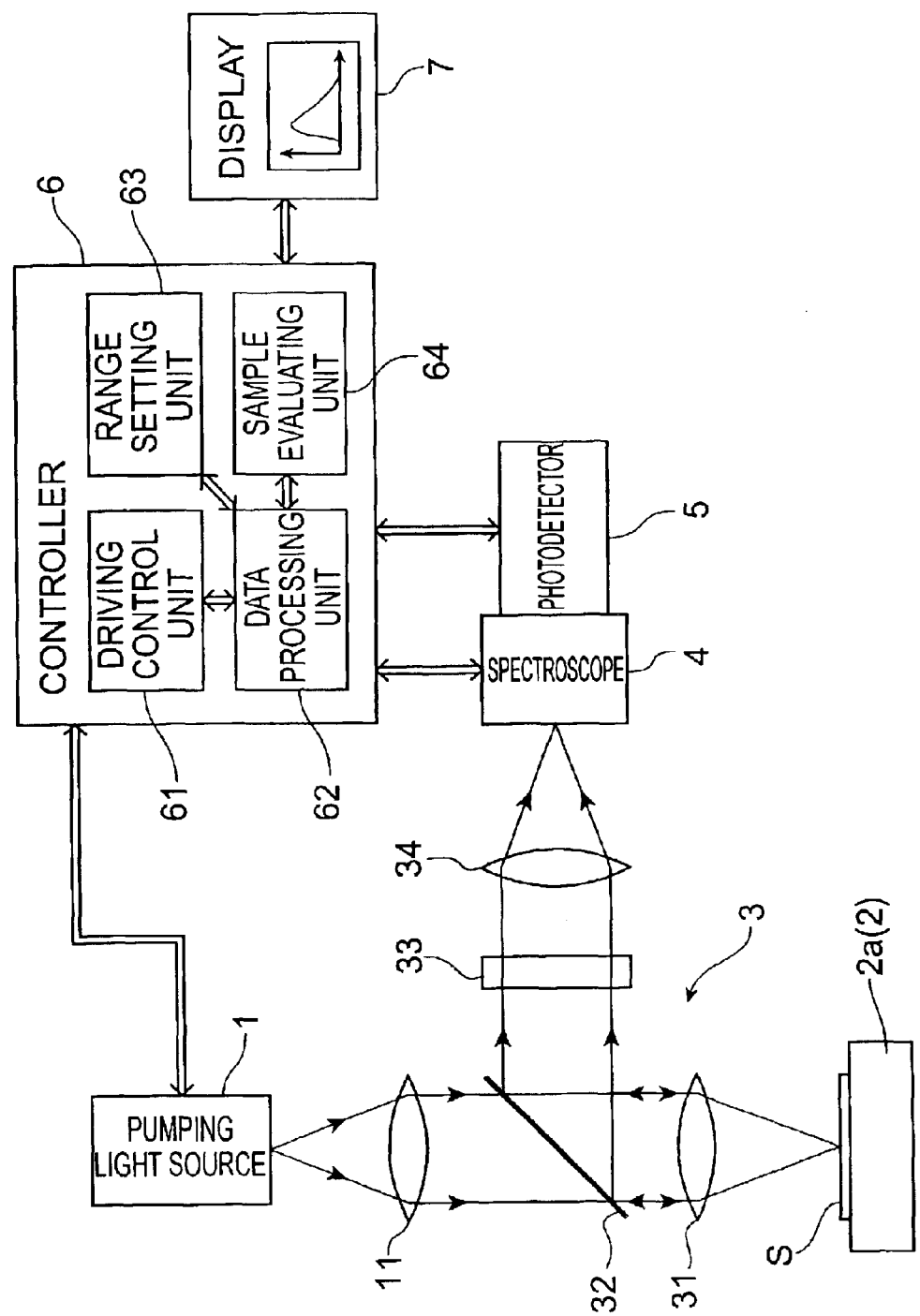
FIG. 7 is a diagram showing an embodiment of sample evaluating apparatus.

FIG. 7 is a diagram showing an embodiment of sample evaluation apparatus using the fluorescence measuring apparatus in accordance with the present invention. In this embodiment, the sample S to be evaluated (e.g., semiconductor wafer) is held in a state mounted on a sample holding table 2a acting as the sample holding means 2.

The pumping light source 1 is placed above the sample S held on the sample holding table 2a, whereas pumping light pulses supplied from the pumping light source 1 pass through a lens 11 and further through a half mirror 32 and a lens 31 which constitute the condensing optical system 3, thereby irradiating a predetermined irradiating position on the sample S which is a part to be evaluated in the sample S. The fluorescence from the part on the sample S pumped with the pumping light pulses is made incident on the photodetector 5 by way of the condensing optical system 3 constituted by the lens 31, half mirror 32, variable optical attenuator 33, and lens 34, and the spectroscope 4 (or wavelength selecting means such as a wavelength selecting filter). Here, the variable optical attenuator 33 is used with its optical attenuation being set as required for adjusting the light quantity when measuring pumping light or fluorescence.

The controller 6 has not only the driving control unit 61, data processing unit 62, and range setting unit 63, but also a sample evaluating unit 64 for evaluating a sample by referring to the result of fluorometry. The functions, operations, and the like of the driving control unit 61, data processing unit 62, and range setting unit 63 are similar to those in the fluorescence measuring apparatus shown in FIG. 1.

On the other hand, the sample evaluating unit 64 compares the measurement waveform data obtained by the data analysis including a plurality of fitting calculations carried out in the data processing unit 62 with reference waveform data determined beforehand. Then, from the results of data comparison, the quality and the like of the part to be evaluated in the sample S are evaluated.

Figure 8:
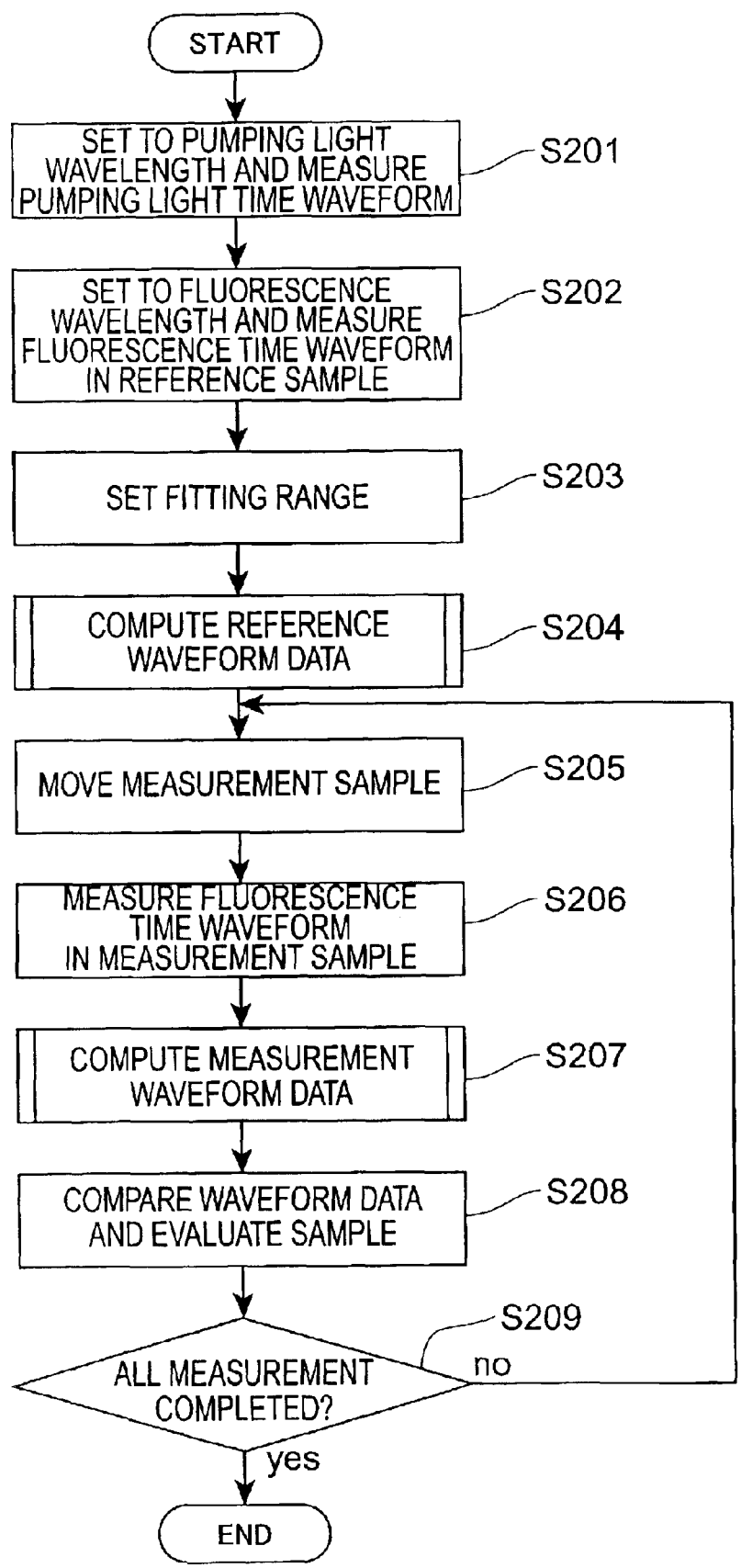
FIG. 8 is a flowchart showing an example of sample evaluating method in the sample evaluating apparatus shown in FIG. 7.

FIG. 8 is a flowchart showing an example of sample evaluation method using the sample evaluating apparatus shown in FIG. 7. The sample evaluating method shown in FIG. 8 illustrates one in which, while moving the sample S in X-Y directions with the sample holding table 2a acting as a movable table, individual parts on the sample S are sequentially irradiated with pumping light pulses from the pumping light source 1, so as to carry out evaluation by fluorometry as in the quality evaluation for each part of a semiconductor wafer or the like.

First, in this sample evaluating method, a pumping light time waveform used for a fitting calculation in a data analysis is carried out (step S201). Here, since the wavelength of pumping light differs from that of fluorescence to be measured, the selecting wavelength region of the spectroscope 4 (or wavelength selecting filter) is switched to the pumping light wavelength and set.

As mentioned above in regard to the fluorescence measuring apparatus of FIG. 1, the measurement of pumping light can be carried out when a scatterer generating no fluorescence is mounted on the sample holding table 2a in place of the sample S. At this time, the quantity of pumping light incident on the photodetector 5 can be adjusted by the variable optical attenuator 33 placed in the condensing optical system 3.

Next, while the wavelength selecting region of the spectroscope 4 (or wavelength selecting filter) is switched to the fluorescence wavelength and set, a reference sample to become a reference for sample evaluation is mounted on the sample holding table 2a, and the fluorescence time waveform in the reference sample is measured (S202). If the fluorescence time waveform in the reference sample has already been measured and prepared, this time waveform data may directly be read out and used without carrying out fluorometry in the reference sample.

Once the fluorescence time waveform in the reference sample is obtained, a fitting range is set with reference to this time waveform (S203). In a specific example of method for setting a fitting range, the fluorescence time waveform in the reference sample is represented on the display 7 connected to the controller 6, and an operator indicates the start and end points of a fitting range by manipulating a mouse cursor or the like. According to thus indicated start and end points, the range setting unit 63 of the controller 6 sets a fitting range employed for the actual measurement of fluorescence that follows. Specifically, a fitting range is fixedly set with respect to the fluorescence time waveform according to the intensity % range with respect to the fluorescence intensity at the fluorescence peak or the time range with respect to the time position of the fluorescence peak.

Next, while employing thus set fitting range, the fluorescence time waveform in the reference sample is subjected to a data analysis including a plurality of fitting calculations in the above-mentioned data analysis method, so as to compute reference waveform data, and the fluorescence lifetime and fluorescence intensity derived therefrom (S204). If the fluorescence time waveform is not shifted, however, a single fitting calculation may be sufficient for computing the reference waveform data.

Once the reference waveform data is obtained, the measurement sample S to be evaluated is placed at a predetermined position on the sample holding table 2a acting as a movable stage, and a sample evaluation by fluorometry is started.

First, the sample holding table 2a is driven, so as to move the measurement sample S such that a predetermined part of the measurement sample S is irradiated with pumping light pulses from the pumping light source 1 (S205), and the fluorescence time waveform in the measurement sample S is measured while pumping light pulses are supplied from the pumping light source 1 (S206). Then, a plurality of fitting calculations in the above-mentioned fitting range are employed, so as to subject thus obtained fluorescence time waveform to a data analysis, thereby computing measurement waveform data, and the fluorescence lifetime and fluorescence intensity derived therefrom (S207).

Subsequently, in the sample evaluating unit 64, the measurement waveform data computed for the measurement sample S is compared with the reference waveform data determined beforehand for the reference sample, so as to evaluate parts of the measurement sample S to be evaluated, thereby determining whether the quality is favorable or not and so forth (S208). As for the comparison between the measurement waveform data and reference waveform data, the waveform data themselves may be compared with each other, or they may be compared with each other in terms of fluorescence lifetime and fluorescence intensity values.

After the sample evaluation is completed, it is investigated whether or not the fluorometry and sample evaluation have been executed for all the evaluating parts of the measurement sample S needed to be evaluated (S209). If they have been executed, all of the fluorometry and sample evaluation for the measurement sample S are terminated. If there are evaluating parts for which the measurement and evaluation have not been executed yet, the measurement sample S is further moved (S205), so as to execute the measurement, computation, and evaluation (S206, S207, S208) repeatedly.

Such a sample evaluating apparatus realizes one which can evaluate a sample accurately and efficiently even when a shift occurs in the fluorescence time waveform. In a semiconductor wafer evaluating apparatus or the like, in particular, a plurality of fluorometric operations are repeatedly executed for individual parts of a sample (semiconductor wafer). When the above-mentioned fluorescence measuring apparatus is employed, influences of time waveform shifts occurring between individual fluorometric operations can be minimized in such a case as well.

Namely, for reducing influences of shifts in fluorescence time waveform along with the lapse of time, the pumping light time waveform can be measured before each of a plurality of fluorometric operations executed. If the pumping light is measured each time as such, the time required for sample evaluation will become longer. In particular, for evaluating the quality of a semiconductor wafer or the like in more detail, an automatic evaluation at a high resolution with a high throughput is required, which necessitates a quite large number of evaluating parts in the whole surface of the semiconductor wafer, thereby increasing the measurement time for sample evaluation.

In the above-mentioned sample evaluating apparatus, by contrast, even when only fluorometry is repeatedly executed with respect to individual parts on the sample after initially measuring the pumping light time waveform, influences of time waveform shifts generated during the fluorometry can be minimized by employing a data analysis effected by a plurality of fitting calculations. Therefore, evaluations of individual parts on the sample can be executed in a short time accurately and efficiently. In particular, since necessary conditions such as the fitting range, the initial position for starting a plurality of fitting calculations, and the like are set beforehand, all of the fluorometry, data analysis, and sample evaluation for individual parts on the measurement sample S can be executed automatically.

Without being restricted to the above-mentioned embodiments, the fluorescence measuring method and apparatus in accordance with the present invention can be modified in various manners. For example, it is preferred that the condensing optical system 3, wavelength selecting means (spectroscope 4), and the like in the apparatus configuration shown in FIG. 1 have their favorable configurations according to the kind of the sample S to be measured, the wavelength of fluorescence, the positional relationship between the pumping light source 1 and photodetector 5, and the like. Though the driving control unit and data processing unit are provided in the same controller 6 in the embodiments shown in FIGS. 1 and 7, they may be disposed as separate driving controller and data processor as well.

As for the measurement of pumping light and fluorescence, the pumping light may be measured after fluorometry, and the above-mentioned data analysis may be carried out for each of their respective time waveforms. Though fluorometry is initially carried out with the reference sample in the flowchart of FIG. 8, setting of a fitting range and the like can be carried out from the fluorescence time waveform obtained by the initial fluorometric operation in the measurement sample without using the reference sample.

As for the arrangement and movement of fluorescence and pumping light time waveforms on the time axis, various data analysis methods can be employed without being restricted to the above-mentioned method executing the fitting calculations while moving the fluorescence time waveform from the initial position to the end position with the pumping light time waveform being arranged at a fixed time position on the time axis.

Namely, more generally, pumping light and fluorescence time waveforms are arranged on the time axis such that a fluorescence peak of the fluorescence time waveform is placed at an initial position earlier or later by a predetermined time width than a time position substantially coinciding with a pumping light peak of the pumping light time waveform, and then, while moving the fluorescence time waveform and fitting range or the pumping light time waveform with respect to the time axis to an end position on the time axis on the opposite side of the time position where the fluorescence peak substantially coincides with the pumping light peak from the initial position, whereby fluorescence measuring method and apparatus which can compute waveform data, individual physical quantities, and the like accurately and efficiency regardless of whether a shift occurs in the fluorescence time waveform or not are obtained.

For example, in the above-mentioned embodiments, as shown in FIGS. 4A to 4D, the fluorescence time waveform F is disposed at the initial position t1 earlier than the pumping light peak (FIG. 4C), and then fitting calculations are carried out while moving the fluorescence time waveform F to the end position t2 (FIG. 4D) later than the pumping light peak. Another data analysis method may be such that the fluorescence time waveform moves from an initial position located at a time position later than the pumping light peak such as the one shown in FIG. 4D to an end position earlier than the pumping light peak. Alternatively, while arranging the fluorescence time waveform F fixedly with respect to the time axis, the pumping light time waveform E can be moved from the initial position to the end position in a similar manner.

However, for simplifying the data analysis procedure, it is preferred that, while one of the pumping light time waveform E and the fluorescence time waveform F is disposed at a fixed position on the time axis, the other be moved with respect to the time axis.

Also, the sample evaluating apparatus can similarly be modified in various manners. For example, in the flowchart shown in FIG. 8, if fluorescence fades in the sample when the fluorescence time waveform is measured (S206), the data analysis (S207) and sample evaluation (S208) may be skipped.

Though the quality evaluation of a semiconductor wafer is explained by way of example as a sample to be evaluated, the present invention can be employed for various other samples as well. For example, fluorescence lifetime measurement, time-resolved fluorescence anisotropy measurement, and the like have been considered effective evaluating means in mask screening, drug screening, and the like carried out while using a microtiter plate or the like as a sample in the process of developing drugs. Automatic evaluations with a high throughput are required in this case as in the semiconductor wafer, whereby employing the sample evaluating apparatus of FIG. 7, the flowchart of FIG. 8, and the like enables efficient sample evaluations.

Industrial Applicability

The fluorescence measuring method and apparatus in accordance with the present invention, and a sample evaluating apparatus using the same can be utilized as fluorescence measuring method and apparatus which can compute waveform data and physical quantities such as fluorescence lifetime efficiently with a sufficient accuracy regardless of whether a shift occurs in the fluorescence time waveform or not, and a sample evaluating apparatus using the same.

Namely, the pumping light and fluorescence time waveforms are arranged at their predetermined time positions with respect to the time axis used for a data analysis for determining a fluorescence lifetime or the like, and a plurality of fitting calculations are carried out while moving the fluorescence time waveform and fitting range or the pumping light time waveform from the initial position where the fluorescence peak is earlier or later by a predetermined time width than the pumping light peak to the end position on the opposite side. Then, from thus determined plurality of waveform data items, an optimal measurement waveform data is selected according to a selection criterion such as the $\chi^2$ value obtained by a fitting calculation. This makes it possible to compute waveform data and physical quantities such as fluorescence lifetime efficiently with a sufficient accuracy regardless of whether a shift occurs in the fluorescence time waveform or not.

Such fluorescence measuring apparatus and sample evaluating apparatus can greatly shorten the time required for measurement and evaluation, in particular, when carrying out a number of fluorometric operations in semiconductor wafer quality evaluations, screening for developing drugs, and the like. Further, since measurement and evaluation become efficient as such, applications are expected to become possible in a wide range with respect to sample evaluations other than the semiconductor wafer evaluation and screening for developing drugs as well.

What is claimed is:

1. A fluorescence measuring method comprising:
    a pumping step of irradiating a sample with pulsed pumping light;
    a light-detecting step of detecting fluorescence released from said sample pumped with said pumping light; and
    a data processing step of subjecting a time waveform of fluorescence detected by said light-detecting step to a data analysis including a fitting calculation in a fitting range serving as a predetermined time range fixedly set for said time waveform of fluorescence so as to compute waveform data, said time waveform of fluorescence having a fluorescence peak;
    wherein said data processing step comprises
    arranging a predetermined time waveform of pumping light having a pumping light peak and said time waveform of fluorescence having said fluorescence peak on a time axis used for said fitting calculation such that said fluorescence peak is placed at an initial position on said time axis that is a predetermined time width earlier or later than a time position substantially coinciding with said pumping light peak, and
    carrying out a fitting calculation at each of a plurality of different time positions on said time axis while moving one of (a) said time waveform of fluorescence and said fitting range, or (b) said time waveform of pumping light, with respect to said time axis, from a start position to an end position on said time axis, said end position being located on a side of said time position where said fluorescence peak substantially coincides with said pumping light peak that is opposite that of the side of said time position where said start position is located, and
    employing a waveform data item selected according to a predetermined selection criterion from a plurality of waveform data items respectively computed in said fitting calculations as final measurement waveform data.

2. A fluorescence measuring method according to claim 1, wherein, in said data processing step, one of said time waveform of pumping light and said time waveform of fluorescence is arranged at a fixed time position on said time axis, and the other is moved with respect to said time axis.

3. A fluorescence measuring method according to claim 1, wherein, in said data processing step, a fluorescence lifetime is determined according to said measurement waveform data.

4. A fluorescence measuring method according to claim 1, wherein, in said data processing step, $\chi^2$ (chi-square) values respectively determined in said fitting calculations are used as said selection criterion, and said waveform data computed in said fitting calculation yielding the minimal $\chi^2$ (chi-suare) value is selected as said measurement waveform data.

5. A fluorescence measuring method according to claim 1, wherein, in said data processing step, a time range set with reference to said fluorescence peak of said time waveform of fluorescence is used as said fitting range.

6. A fluorescence measuring method according to claim 1, further comprising a range setting step of setting said fitting range prior to said pumping step.

7. A fluorescence measuring apparatus comprising:
    pumping means for irradiating a sample with pulsed pumping light;
    light-detecting means for detecting fluorescence released from said sample pumped with said pumping light; and
    data processing means for subjecting a time waveform of fluorescence detected by said light-detecting means to a data analysis including a fitting calculation in a fitting range serving as a predetermined time range fixedly set for said time waveform of fluorescence so as to compute waveform data, said time waveform of fluorescence having a fluorescence peak;
    wherein said data processing means
    arranges a predetermined time waveform of pumping light having a pumping light peak and said time waveform of fluorescence having said fluorescence peak on a time axis used for said fitting calculation such that said fluorescence peak is placed at an initial position on said time axis that is a predetermined time width earlier or later than a time position substantially coinciding with said pumping light peak, and carries out a fitting calculation at each of a plurality of different time postions on said time axis while moving one of (a) said time waveform of fluorescence and said fitting range or (b) said time waveform of pumping light, with respect to said time axis, from a start position to an end position on said time axis, said end position being located on a side of said time position where said fluorescence peak substantially coincides with said pumping light peak that is opposite that of the side of said time position where said start position is located, and employs a waveform data item selected according to a predetermined selection criterion from a plurality of waveform data items respectively computed in said fitting calculations as final measurement waveform data.

8. A fluorescence measuring apparatus according to claim 7, wherein said data processing means arranges one of said time waveform of pumping light and said time waveform of fluorescence at a fixed time position on said time axis and moves the other with respect to said time axis.

9. A fluorescence measuring apparatus according to claim 7, wherein said data processing means determines a fluorescence lifetime according to said measurement waveform data.

10. A fluorescence measuring apparatus according to claim 7, wherein said data processing means uses $\chi^2$ (chi-square) values respectively determined in said fitting calculations as said selection criterion, and selects said waveform data computed in said fitting calculation yielding the minimal $\chi^2$ (chi-square) value as said measurement waveform data.

11. A fluorescence measuring apparatus according to claim 7, wherein said data processing means uses a time range set with reference to said fluorescence peak of said time waveform of fluorescence as said fitting range.

12. A fluorescence measuring apparatus according to claim 7, further comprising range setting means for setting said fitting range beforehand.

13. A sample evaluating apparatus comprising:

the fluorescence measuring apparatus according to claim 7; and sample evaluating means for evaluating said sample by comparing said measurement waveform data obtained in said data processing means of said fluorescence measuring apparatus and reference waveform data determined beforehand with each other.

* * * * *